United States Patent [19]

Newsome et al.

[11] 4,332,814
[45] Jun. 1, 1982

[54] TREATMENT OF DIARRHOEA

[75] Inventors: Peter M. Newsome, Worcester Park; Noel A. Mullen, Cranleigh, both of England

[73] Assignee: Beecham Group Limited, England

[21] Appl. No.: 177,365

[22] Filed: Aug. 11, 1980

[30] Foreign Application Priority Data

Aug. 23, 1979 [GB] United Kingdom ............... 7929434

[51] Int. Cl.$^3$ ............... A61K 31/415; A61K 31/165
[52] U.S. Cl. ............................... 424/273 R; 424/324
[58] Field of Search ........................... 424/273 R, 324

[56] References Cited

FOREIGN PATENT DOCUMENTS 1072962 4/1980 Canada.

OTHER PUBLICATIONS

Douglas—Chem. Abst., vol. 91, (1979), p. 74,365y.
Kleinlogel et al.—Chem. Abst., vol. 84, (1976), p. 54,179t.
Minker et al.—Chem. Abst., vol. 88, (1978), p. 183,383m.
Douglas et al.—Arzn.-Forsch/Drug Res. 28(11), Heft 8a, (1978), pp. 1435–1440.
Riley et al.—Arzn.-Forsch/Drug Res. 28(11), Heft 8a, (1978), p. 1461.
Mir et al.—Arzn.-Forsch/Drug Res. 28(11), Heft 8a, (1978), pp. 1448–1454.

Primary Examiner—Sam Rosen
Attorney, Agent, or Firm—Jacobs & Jacobs

[57] ABSTRACT

Vasoconstrictor α-adrenergic agonists of formula (I)

$$A—B—C \qquad (I)$$

wherein, A is a 2-imidazoline group or a guanidine group; B is a chemical bond or a linking group one or two atoms in length; and C is a $C_{6-10}$ mono- or bi-cyclic group which is either an aromatic group, a heteroaromatic group containing only one hetero-atom, or a group containing an aromatic moiety; and which group C may be substituted by $C_{1-4}$ alkyl, $C_{1-4}$ alkoxy, halogen or hydroxyl; or salts thereof, are useful in the treatment and prevention of diarrhoea in livestock. Compositions of these compounds are described.

7 Claims, No Drawings

TREATMENT OF DIARRHOEA

This invention relates to the treatment of diarrhoea in livestock, such as cattle and pigs.

More specifically, this invention relates to the use of a class of α-adrenergic agonists in the treatment of diarrhoea in livestock.

Diarrhoea (also referred to as scours) in livestock can be a severe disease in young animals and can even result in death. The diarrhoea frequently involves colonisation of the small intestine with enteropathogenic strains of E. coli which produce heat stable and/or heat labile enterotoxins. These enterotoxins stimulate fluid secretion in the gut lumen and hence cause diarrhoea. The associated fluid loss may lead to loss of condition, reduced weight gain and often to death. A class of compounds has now been discovered which is effective in the therapy of diarrhoea of this nature.

It should be pointed out that many of the compounds making up this class are known as vasoconstrictors in man, and indeed some of the compounds have been used commercially as nasal decongestants. One of the compounds, Tetrahydrozoline, was disclosed in U.S. Pat. No. 2,842,478 as a potentiator for CNS depressants, as was its use in combination with a CNS depressant for the therapy of animals. However, in this Patent, which was published over twenty years ago, there is no suggestion that Tetrahydrozoline could be used for treating the above described specific type of diarrhoea, and in the Patent it is believed clear that the animals to be treated were pets such as cats and the like, not livestock such as cattle and pigs as in this invention.

It should also perhaps be mentioned that certain compounds of our class were tested primarily for their effects on blood pressure in a paper by Hartmann and Isler, Arch. Exp. Path. Pharmakol, 1939, 192, pages 141-154. In this paper, it is mentioned that some of the compounds have an inhibitory effect on the isolated rabbit intestine. However in the summary of the paper no mention of these results is made, as it is quite clear that the major emphasis of the paper is on blood pressure effects, and of course no suggestion is made that these results might render the compounds of any use in the treatment of diarrhoea, let alone in the treatment of toxin stimulated diarrhoea the therapy of which forms the basis of the present invention. It is believed that the fact that this paper is forty years old, and that to our knowledge no disclosure has since been made to the effect that relevant compounds described in the paper could be used in diarrhoea therapy, clearly demonstrates that the paper provides no teaching for this use of the compounds.

Accordingly, in one aspect, this invention provides a method of treating diarrhoea in livestock, which method comprises administering to the sufferer a compound characterised in being an α-adrenergic agonist having vasoconstrictor activity, and also characterised in having the formula (I):

A-B-C  (I)

wherein:

A is a 2-imidazoline group, or a guanidine group;

B is a chemical bond, or a linking group one or two atoms in length; and

C is a $C_{6-10}$ mono or bi-cyclic group which is either an aromatic group, a heteroaromatic group containing only one heteroatom, or a group containing an aromatic moiety; and which group may be substituted by $C_{1-4}$ alkyl, $C_{1-4}$ alkoxy, halogen or hydroxy; or a salt thereof.

The compound to be administered must meet the three requirements of this invention.

Firstly, the compound must be an α-adrenergic agonist. As is well known, α-adrenergic agonists are compounds which interact with a sub-class of cellular receptors for noradrenaline (α-receptors) and as a result elicit pharmacological actions characteristics of those receptors-see for example R. P. Ahlquist, Am. J. Physiol. 153, 536 (1948).

Secondly, the compound must be a vasoconstrictor. As is well known, vasoconstrictors are compounds which increase peripheral resistance to blood flow by contracting vascular smooth muscle.

Thirdly, of course, the compound must be of the formula (I).

To the skilled man it will be a simple matter to identify compounds meeting these three requirements. Of course many known compounds are also known to have the necessary α-agonist and vasoconstrictor activities, and thus no further work will be needed in identifying such compounds for use in our invention. Whether a given novel compound, or a given known compound of unknown α-agonist and/or vasoconstrictor activity, may be used in our invention is simply determined by routine pharmacological testing.

Examples of suitable known compounds include:

Naphazoline 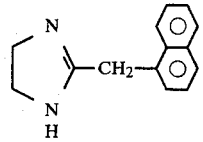

Tymazoline 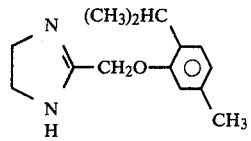

Phedrazine 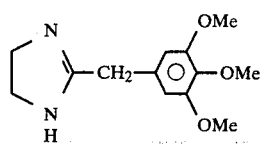

Tetrahydrozoline 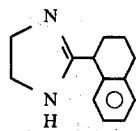

Xylometazoline 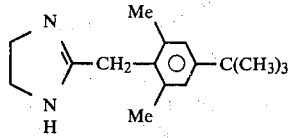

Oxymetazoline 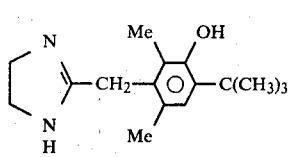

-continued

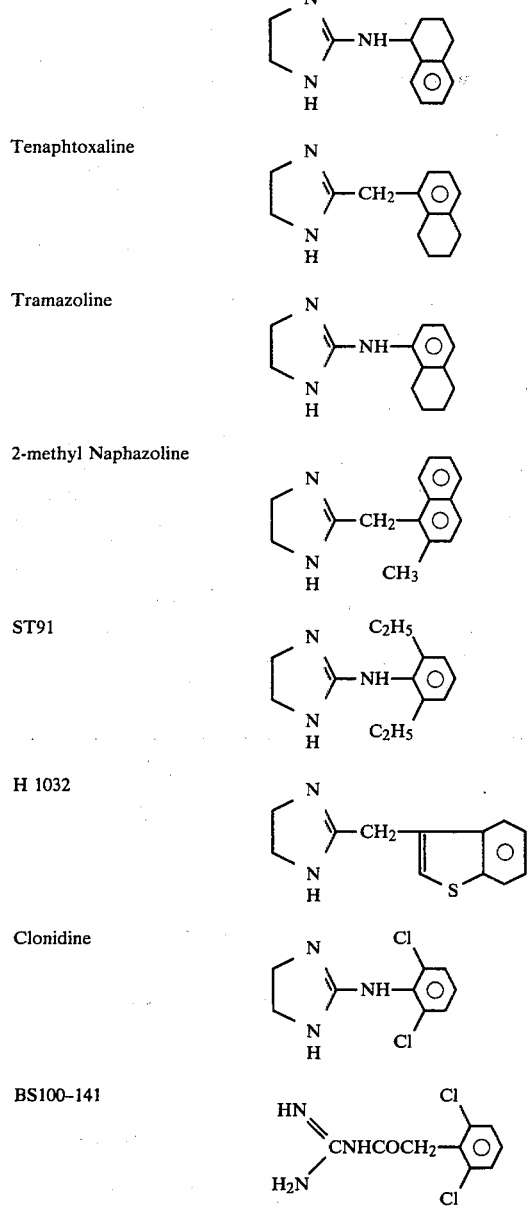

It will be appreciated from the foregoing that suitable examples of the feature B in the α-agonist vasoconstrictors of this invention include —CH₂—, —CO—CH₂—, —CH₂O—, —NH—, and a direct chemical bond. Preferred examples of B include —CH₂—, —NH— and —CO—CH₂—.

Similarly, suitable examples of the $C_{6-10}$ mono- or bi-cyclic group in C in the α-agonist vasoconstrictor of this invention include aromatic groups such as phenyl and naphthyl; partially aromatic groups such as tetrahydronaphthyl; and heteroaromatic groups such as benzothienyl. Preferred examples of this group include phenyl and naphthyl.

Suitable examples of optional substituents for the $C_{6-10}$ mono- or bi-cyclic group in C include methyl, iso-propyl, methoxy, hydroxy and chloro. Often, if present, there will be two to four of such substituents in C. When C is substituted phenyl, preferred examples of such groups include those in which one or two of the above named substituents are ortho to the feature B.

In use, the α-agonist vasoconstrictors will be administered in the form of compositions.

Thus one important aspect of this invention provides a veterinary composition for the treatment of diarrhoea in livestock, which composition comprises a compound of the formula (I) as hereinbefore defined and a veterinarily acceptable carrier.

This composition will, of course, be adapted for administration to livestock such as cattle or pigs, preferably to young cattle or pigs.

Thus for example the composition may be a shaped composition, such as a bolus, tablet or capsule. In such cases of course the veterinarily acceptable carrier will be chosen from the usual range of lubricants, dispersants, binders, fillers and the like. As these shaped compositions are for administration to livestock, often they will weigh at least 1 g, on occasions at least 2 g.

The composition may also be a dispersion or a solution of the drug in a suitable vehicle for use with an oral doser (this is a well known item of farm equipment, basically comprising a liquid reservoir, a mouthpiece adapted for insertion into animal mouths, and a pump mechanism whereby unit doses can be ejected from the reservoir through the mouthpiece). Conveniently the vehicle will be an oil or water based cream to ensure homogeneity of the unit doses administered.

The invention therefore also provides an oral doser containing a multi-dose of a compound of the formula (I) in a veterinarily acceptable vehicle.

The compounds of the invention may also be added to the animal feed or drinking water. Thus the invention also provides animal feed or animal drinking water containing a compound of the formula (I). It will be convenient to formulate these animal feed and animal drinking water compositions with a multi-dose of the drug so that the animal takes in an appropriate quantity of the drug along with its diet.

With young animals, a particularly useful technique is to blend their milk with the drugs of this invention.

It will also be convenient to present the compositions of the invention as pre-mixes for addition to the feed or drinking water.

The compositions of the invention may also be formulated for injection. In such cases the drug chosen is suitably dissolved in water for injection together with agents to adjust tonicity is necessary.

Often it will be appropriate to include in the hereinbefore described compositions a further veterinary medicine such as an anti-bacterial agent, for example amoxycillin.

Also, it is believed that the compounds of this invention can usefully be combined with the oral rehydration composition described in U.S. Pat. No. 4,164,568.

It will be appreciated that the effective dose of the compounds of the formula (I) will depend in the usual way upon factors such as the severity of the diarrhoea, the weight of the sufferer, the particular compound chosen, and on similar variables. However, as a rough guide we believe that a suitable dose will be within the range 0.05 to 10 mg/kg, which dose may be repeated as and when required.

Clearly the compositions of the invention will contain sufficient compound to enable this effective dose to be administered in convenient manner. Thus by way of example useful dosage units of the composition may contain 0.05 to 500 mg of the compound, more suitably 0.5 to 400 mg. Of course, it will be appreciated that many preferred compositions of the invention are in multi-dose form, as for the therapy of animals it is often most desirable to be able rapidly to treat a number of animals. Such multi-dose compositions will contain by way of example at least 1 g of the compound. Depending on the exact nature of the said multi-dose composition, often it will contain at least 5 g of the compound, and on occasions as much as 20 g.

The following Examples illustrate the anti-diarrhoeal activity of the compounds, and their formulation into veterinary compositions.

BIOLOGICAL EVALUATION OF THE COMPOUNDS

The following tests were carried out:

1. Mice Infant mice are separated from their mothers shortly before use. Animals up to 15 l days of age are suitable for use but we normally use animals 7–9 days of age. Groups of animals are dosed with the compound 45 mins prior to oral challenge with 0.05–0.10 ml of culture filtrate prepared from an enteropathogenic strain of *E. coli*. Control animals receive drug vehicle 45 mins prior to challenge with a similar amount of culture filtrate. The compounds are administered orally. Animals are killed two hours later and the entire intestine removed. The ratio of gut weight to remaining bodyweight (GW/BW) is determined from each animal and the increase in this ratio is determined by subtracting 0.06 (GW/BW for untreated mice) from the GW/BW of the animal. Drug treated animals are compared with untreated controls. If the compound has had an effect in inhibiting the fluid secretion caused by the enterotoxin(s) present in the culture filtrate then the gut weight/bodyweight ratio should be reduced in the treated animals. The percentage fluid inhibition is determined from the formula:

$$100 - \left[ \frac{\text{Mean increase in } GW/BW \text{ ratio in treated animals}}{\text{Mean increase in } GW/BW \text{ ratio in control animals}} \right] \times 100$$

2. Rabbits

Infant rabbits 7–10 days old are dosed with the compound under investigation orally 45 min prior to oral challenge with 50 ml/kg bodyweight of material prepared by cell lysis of an enteropathogenic strain of *E. coli*. Control animals receive drug vehicle 45 mins prior to challenge with a similar volume of material. 5–7 Hours after oral administration of the challenge the animals are killed and gut weight/remaining bodyweight ratios calculated and the percentage fluid inhibition determined as above.

3. Piglets

2–4 Day old piglets are dosed with the compound orally 45 min prior to oral challenge with 25 ml of culture filtrate prepared from an enteropathogenic strain of *E. coli*. Control animals receive drug vehicle 45 min prior to challenge with a similar volume of material. Animals are observed for diarrhoea over a 7 hour period and the severity of scour scored on a 0–3 basis for each animal at hourly intervals. The percentage inhibition in treated animals is determined as:

$$100 - \left[ \frac{\text{Mean score of scour in treated animals}}{\text{Mean score of scour in control animals}} \times 100 \right]$$

Results obtained are given in the Table.

| Compound* | Structure | Mouse Dose mg/kg | Mouse % Fluid Inhibition | Rabbit Dose mg/kg | Rabbit % Fluid Inhibition | Piglet Dose mg/kg | Piglet % Fluid Inhibition |
|---|---|---|---|---|---|---|---|
| Naphazoline | | 10 | 59 | 10 | 32 | 10 | 88 |
| Oxymetazoline | | 0.1 | 78 | | | | |
| Xylometazoline | | 8.25 | 44 | 20 | 119 | 2 | 44 |
| Tramazoline | | 10 | 44 | | | | |
| Clonidine | | 1 | 42 | 5 | 26 | 0.2 | 64 |

-continued

| Compound* | Structure | Screen Mouse Dose mg/kg | Mouse % Fluid Inhibition | Rabbit Dose mg/kg | Rabbit % Fluid Inhibition | Piglet Dose mg/kg | Piglet % Fluid Inhibition |
|---|---|---|---|---|---|---|---|
| BS 100–141 | (structure: HN=C(NH₂)–NHCOCH₂–(2,6-dichlorophenoxy)) | 1 | 45 | | | 1 | 76 |
| Lidamidine | (structure: CH₃HN–C(=NH)–NH–CO–NH–(2,6-dimethylphenyl)) | 50 | 33 | 50 | −7 | | |
| 2-Methyl Naphazoline | (structure: imidazoline–CH₂–(2-methylnaphthyl)) | 20 | 82 | | | | |
| ST91 | (structure: imidazoline–NH–(2,6-diethylphenyl)) | 5 / 1 | 56 / 22 | | | | |

*All compounds tested as hydrochloride salts

These results clearly demonstrate the high level of activity of the Compounds in the reduction of fluid secretion caused by challenge with an enterotoxin from an enteropathogenic strain of *E. coli*.

The activity of the Compounds is highlighted by comparison with Lidamidine, which as can be seen from the Table, is at least five times less active than the Compounds in the mouse test and inactive in the rabbit test.

Lidamidine is a known anti-diarrhoeal, for example as reported in G. N. Mir et. al., Arzneim-Forsch/Drug Res 28 (II), Heft 8a (1978), page 1448, wherein it was alleged inter alia that Lidamidine inhibited intestinal secretion induced by cholera toxin.

A number of compounds allegedly structurally related to Lidamidine, as well as Lidamidine itself, were examined for various pharmacological acitivities in G. H. Douglas et. al., Arzneim-Forsch/Drug Res. 28 (II), Heft 8a (1978), page 1435. These activities included an anti-diarrhoeal test, but no evidence was presented in this paper in relation to diarrhoea caused by toxin induced intestinal secretion.

4. Anti-diarrhoeal Effect in *E. coli* Infected Piglets

Colostrum deprived piglets were infected on the first day of life with *E. coli* P155 by oral administration of approximately $3 \times 10^9$ organisms. When scour was observed the animals were paired by weight and severity of scour and one animal from each pair was treated with amoxycillin 40 mg p. o. whilst the other animal was treated with 40 mg p. o.+2 mg/Kg p. o. naphazoline hydrochloride in water. The water and naphazoline hydrochloride solutions were coded and dosing and scoring of the severity of diarrhoea were carried out "Blind" as described in the experiments with enterotoxin induced diarrhoea (above).

The following result was obtained:

| | Mean scour score ± S.E.M. (during 6 hrs after treatment) |
|---|---|
| Amoxycillin + water | 2.0 ± 0.2 (n = 14) |
| Amoxycillin + naphazoline HCL | 0.8 ± 0.1 (n = 14) |

The result was statistically significant $P<0.001$ (t test

5. Calf Thiry-Vella Intestinal Loop Model

In vivo tests were conducted using male castrate calves, each with two surgically prepared Thiry-Vella intestinal loops prepared as described by R. J. Bywater, J. Comp. Path., 80, 565, (1970).

The loops are washed with saline and then a saline bolus is left in the loops for 30 minutes to establish a basal absorptive rate. After 30 minutes the fluid in the loops is removed and measured. Heat stable *E. coli* enterotoxin from *E. coli* strain p16 is added to the loop infusate which is then returned to the loops.

After a further 30 minutes the content of the loops is measured once more and at this time the drug is added to the test loop perfusate.

TOXICITY

The compounds have been found to have a satisfactory therapeutic ratio.

| Inhibition of Toxin Induced Intestinal Secretion in Calf Thiry-Vella Loops | | | | | | | |
|---|---|---|---|---|---|---|---|
| Time (Min. after toxin administration | Control | Naphazoline 2mg/Kg | Control | Clonidine 10µg/Kg | Clonidine 0.8µg/Kg | Control | BS100–141 1µg/Kg |
| −30–0 | −9 | −7 | −4 | −5 | −2 | −4 | −4 |
| 0–30 | 24 | 25 | 22 | 20 | 21 | 34 | 36 |

-continued

| Inhibition of Toxin Induced Intestinal Secretion in Calf Thiry-Vella Loops | | | | | | | |
|---|---|---|---|---|---|---|---|
| Time (Min. after toxin administration | Control | Naphazoline 2mg/Kg | Control | Clonidine 10μg/Kg | Clonidine 0.8μg/Kg | Control | BS100-141 1μg/Kg |
| 30-60 | 24 | 1* | 16 | 2* | 5* | 25 | 13* |
| 60-90 | 20 | 3* | 11 | −1* | 3* | 17 | 10* |
| 90-120 |  |  | 8 | −3* | 1* | 15 | 8* |
| 120-150 |  |  | 8 | −3* | 2* | 13 | 8 |

*indicates statistical significance at least at the 5% level (paired t test.)

FORMULATION OF THE COMPOUNDS FOR VETERINARY ADMINISTRATION

EXAMPLE 1

*Naphazoline bolus 10 mg*

Boluses of the following composition were prepared:

| | |
|---|---|
| Naphazoline hydrochloride | 10 mg |
| Microcrystalline cellulose | 500 mg |
| Corn starch | 250 mg |
| Magnesium stearate | 25 mg |
| Lactose, anhydrous | to 2500 mg |

The ingredients were passed through a 30 mesh stainless steel screen and blended in a suitable blender. The resultant compression mix was compressed directly on a tabletting machine to give tablets each containing 10 mg naphazoline hydrochloride.

EXAMPLE 2

Xylometazoline Oral Doser 1 mg/g

1 Kg of the following composition was prepared:

| | % by wt. |
|---|---|
| Xylometazoline hydrochloride | 0.1 |
| Aluminium stearate | 6.0 |
| Sunflower oil | to 100 |

The aluminium stearate was dispersed with stirring in a portion of the sunflower oil heated to 115° C. The dispersion was added to the rest of the sunflower oil heated to 140° C. The gel was stirred at 130° C. for 15 minutes and then allowed to cool without stirring to room temperature. The milled xylometazoline hydrochloride was dispersed in the cooled gel base and then passed through a colloid mill to produce a fine, homogenous dispersion. The dispersion was filled into plastic bottles fitted with a dosing pump.

EXAMPLE 3

Clonidine Injection 0.5 mg/ml

1 Liter of the following composition was prepared:

| | % w/v |
|---|---|
| Clonidine hydrochloride | 0.05 |
| Sodium chloride | 0.5 |
| Water for injections | to 100 |

The clonidine hydrochloride and sodium chloride were dissolved in the water for injections and the solution as filtered and filled into glass ampoules. The ampoules were sterilised by autoclaving.

EXAMPLE 4

BS 100-141 Premix

A premix of the following composition was prepared:

| | % by wt. |
|---|---|
| BS 100-141 (2,6-dichlorophenylacetylguanidine hydrochloride) | 1.0 |
| Limestone flour | to 100 |

The ingredients were mixed together in a ribbon blender to give a homogenous mixture. The premix was mixed into animal feed at the rate of 1 kg per metric ton to provide a concentration of 10 g of BS 100-141 per metric ton.

EXAMPLE 5

Naphazoline Soluble Powder

1 Kg of the following composition was prepared:

| | % by wt |
|---|---|
| Naphazoline hydrochloride | 13.6 |
| Lactose | to 100 |

The naphazoline hydrochloride and lactose were sieved and mixed together in a suitable blender to give a homogenous powder. The powder was filled into jars. The powder was used at the rate 0.5 g per gallon of drinking water to medicate pigs.

We claim:

1. A method for treating diarrhoea in livestock, which comprises administering to livestock an amount effective to treat diarrhoea of a compound which is an α-adrenergic agonist and which has vasoconstrictor activity and is further characterized by formula (I):

$$A-B-C \qquad (I)$$

wherein
A is 2-imidazolinyl or guanidinyl;
B is selected from a direct bond, $-CH_2-$, $-CH_2O-$, $-COCH_2-$ or $-NH-$; and
C is phenyl, naphthyl, tetrahydronaphthyl or benzothienyl, unsubstituted or substituted by $C_{1-4}$ alkyl, $C_{1-4}$ alkoxy, halogen or hydroxy, or a salt thereof.

2. The method according to claim 1, wherein the compound of formula (I) is administered as a veterinary composition in association with a veterinarily acceptable carrier.

3. The method according to claim 1, wherein said compound of formula (I) is selected from the group consisting of

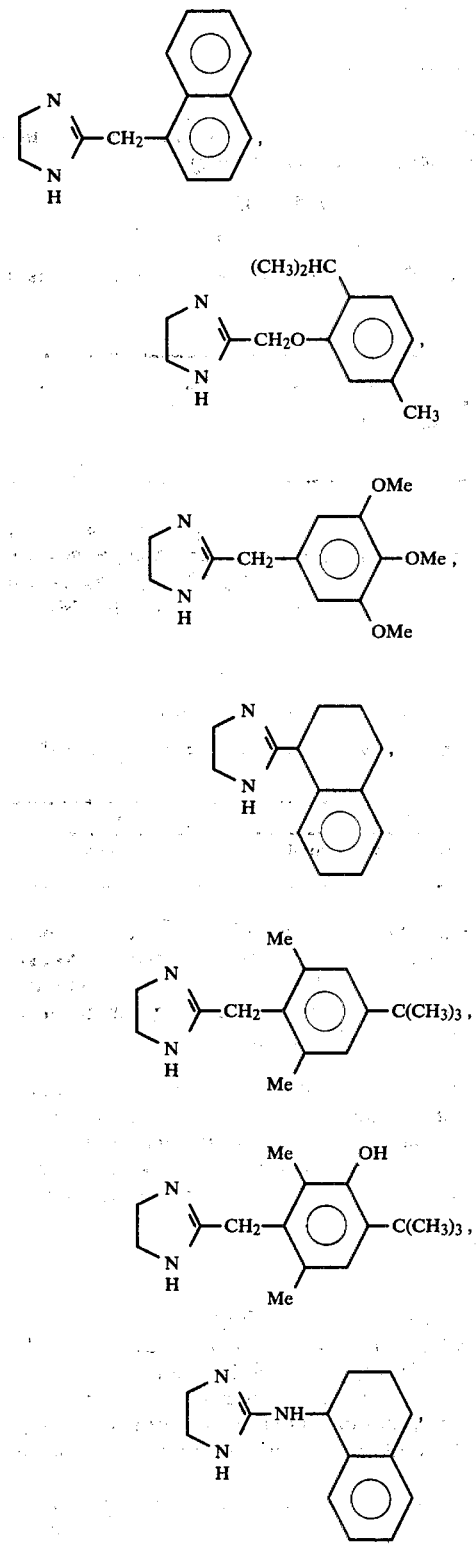

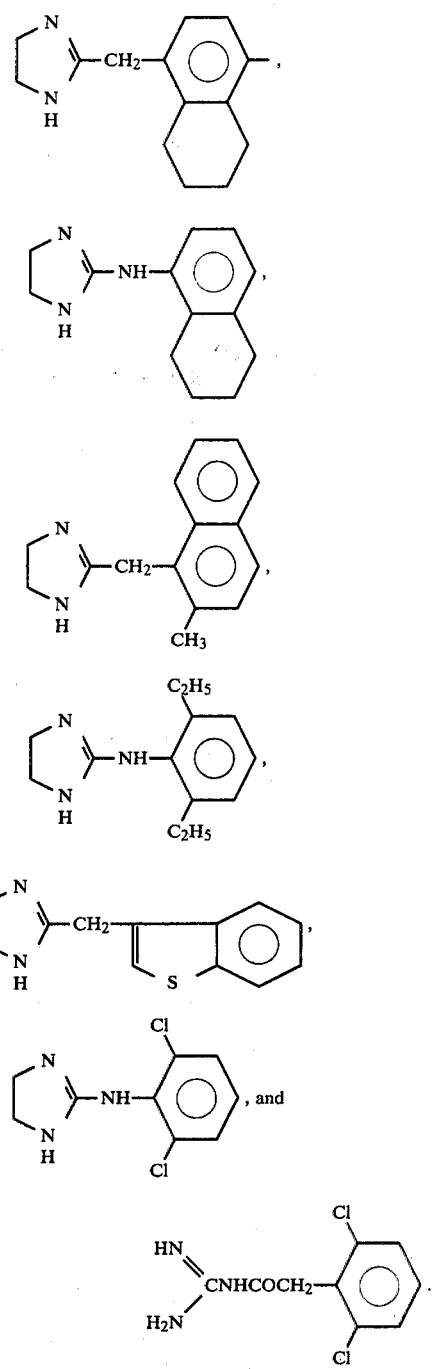

4. The method according to claim 1, wherein said compound of formula (I) is administered in foodstuff or drinking water provided for the livestock.

5. The method according to claim 2, wherein said carrier is an orally administrable oil or water based cream.

6. The method according to claim 2, wherein said compound of formula (I) is administered in water by injection.

7. The method according to claim 2, wherein said compound of formula (I) is administered in multidosage form containing at least 5 g. of said compound.

* * * * *